United States Patent [19]

Sousa

[11] Patent Number: 4,613,617
[45] Date of Patent: Sep. 23, 1986

[54] SYNERGISTIC INSECTICIDAL COMPOSITIONS CONTAINING DIONE ESTERS

[75] Inventor: Anthony A. Sousa, St. Albans, W. Va.

[73] Assignee: Union Carbide Corporation, Danbury, Conn.

[21] Appl. No.: 724,960

[22] Filed: Apr. 23, 1985

Related U.S. Application Data

[63] Continuation of Ser. No. 277,731, Jun. 26, 1981, abandoned.

[51] Int. Cl.[4] ...................... A01N 37/34; A01N 53/00
[52] U.S. Cl. ..................................... 514/521; 514/531
[58] Field of Search ................. 514/521, 531; 424/304

[56] References Cited

U.S. PATENT DOCUMENTS

| 3,835,176 | 9/1974 | Matsuo et al. | 424/304 |
| 4,175,135 | 11/1979 | Haines | 424/311 |
| 4,209,532 | 6/1980 | Wheeler | 424/304 |
| 4,218,469 | 8/1980 | Fuchs et al. | 424/304 |

Primary Examiner—Douglas W. Robinson
Attorney, Agent, or Firm—Gerald L. Coon

[57] ABSTRACT

Insecticidal compositions are provided which contain dione esters in admixture with other insecticides such as pyrethroid, carbamate or organophosphates. The use of the compositions of this invention provides synergistic kill of insects.

10 Claims, No Drawings

SYNERGISTIC INSECTICIDAL COMPOSITIONS CONTAINING DIONE ESTERS

This application is a continuation of prior U.S. application Ser. No. 277,731 filed June 26, 1981, now abandoned.

This invention relates, in general, to synergistic insecticidal compositions. In one aspect, this invention relates to compositions which contain dione esters in admixture with other insecticides, such as, pyrethroid, carbamate or organophosphates. In a further aspect, this invention relates to a method of controlling insects by application of insecticidally effective amounts of synergistic compositions which comprise a pyrethroid, a carbamate or an organophosphate insecticide and a synergistically effective amount of esters of 2-aryl-1,3-cyclohexandione.

Prior to the present invention it was known that combinations of pyrethroids and certain pesticides provided synergistic kill of arthropods. For example, in U.S. Pat. No. 4,144,331 there is disclosed synergistic combinations containing chlorofenvinphos and esters of carboxylic acids which are indicated to be useful for the control of diptera and ticks. Synergistic pesticidal compositions are also described in the literature which are comprised of a pyrethroid insecticide and N,N-(2,4-dixylyliminomethyl)-methylamine. The prior art also teaches that mixtures of certain other pesticides provide synergistic kill of arthropods. For example, Belgian Pat. No. 849,275 discloses the use of mixtures of sulprophos and chlordimeform.

Although the aforementioned combinations of pesticidal compositions were reported to have synergistic kill, the combinations were comprised of the specific components disclosed. No extension to other pesticidal combinations was suggested. In fact, to find specific combinations among the many thousands of biologically active compounds which would possess synergistic kill of pesticides, by a trial and error approach would be beyond the realm of even the most sophisticated research laboratories. However, it was unexpectedly and surprisingly found that compositions which contain certain dione esters in admixture with pyrethroids, carbamates or organophosphates, provided synergistic kill of insects.

Accordingly, one or more of the following objects can be achieved by the practice of this invention. It is an object of this invention to provide insecticidal compositions which contain dione esters in admixture with other insecticides. It is another object of this invention to provide insecticidal compositions comprised of dione esters and insecticides such as pyrethroids, carbamates or organophosphates. A further object is to provide insecticidal compositions which have synergistic kill of insects. A still further object of this invention is to provide a method for controlling pests by applying pesticidally effective amounts of the compositions of this invention.

These and other objects will readily become apparent to those skilled in the art in the light of the teachings herein set forth.

In a broad aspect, this invention is directed to synergistic insecticidal compositions which are characterized by the presence of a dione ester. The ester employed in the present invention has the generic formula:

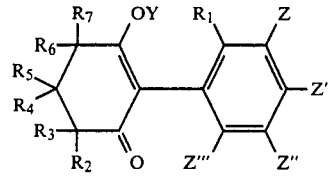

wherein:
Z, Z', Z" and Z''' are individually hydrogen, haloalkyl, polyhaloalkyl, halogen, alkyl, alkoxy, cyano, nitro, alkylthio, alkylsulfinyl, alkylsulfonyl, alkanoyl, amido or amino;

Y is

R is hydrogen, halogen, alkyl, alkenyl, alkynyl, bicycloalkyl, bicycloalkenyl, cycloalkyl, cycloalkenyl, haloalkyl, phenyl, phenylalkyl, naphthyl or naphthylalkyl, all of which, other than hydrogen and halogen, may be substituted with one or more alkyl, cyano, nitro, alkoxy, halogen, haloalkyl, alkylthio, alkylsulfinyl, alkylsulfonyl, alkoxyalkyl, alkylthioalkyl, alkylsulfinylalkyl, alkylsulfonylalkyl or dialkylamino substituents.

$R_1$ is alkyl, polyhaloalkyl or haloalkyl or halogen;

$R_2$, $R_3$, $R_4$, $R_5$, $R_6$ and $R_7$ are individually hydrogen or either substituted or unsubstituted alkyl or phenyl, wherein the permissible substituents are one or more alkyl, cyano, halogen, nitro, alkoxy, alkylthio, alkylsulfinyl, alkylsulfonyl or dialkylamino substituents; or any two $R_2$, $R_3$, $R_4$, $R_5$, $R_6$ or $R_7$ substituents together may form an alkylene or alkenylene chain having from 2 to 20 carbon atoms completing a 3, 4, 5, 6 or 7 membered ring structure;

with the proviso that $R_1$, $R_2$, $R_3$, $R_4$, $R_5$, $R_6$, $R_7$, Z, Z', Z", and Z''' individually may not include more than ten aliphatic carbon atoms and R may not include more than thirty aliphatic carbon atoms.

Illustrative compositions encompassed by the above generic formula are:

2-(2'-Chlorophenyl)-3-(7-phenylheptanoyloxy)-5,5-dimethyl-2-cyclohexenone 2-(2'-Chlorophenyl)-3-(2',6'-dichlorohexanoyloxy)-2-cyclohexenone 2-(2'-4'-Dibromophenyl)-3-(hexanoyloxy)-2-cyclohexenone 2-(2'-Chlorophenyl)-3-(2-ethylhexanoyloxy)-2-cyclohexenone 3-(2'-Isopropylphenyl)-3-acetoxy-spiro[5.5]undec-3-en-2-one.

2-(2'-Chlorophenyl)-3-benzoyloxy-5,5-dimethyl-2-cyclohexenone 2-(2'-Bromophenyl)-3-(4'-chlorobenzoyloxy)-5,5-dimethyl-2-cyclohexenone 2-(2'-Chlorophenyl-3-(5'-diethylaminophenylcarbonyloxy)-5,5-dimethyl-2-cyclohexenone 2-(2'-Chlorophenyl)-3-(4'-chlorophenylcarbonyloxy)5,5-dimethyl-2-cyclohexenone 2-(2'-Chlorophenyl)-3-(4'-methylthiophenylcarbonyloxy)-5,5-dimethyl-2-cyclohexenone 2-(2'-chloro-5'-Nitrophenyl)-3-(4'-dimethylaminophenylcarbonyloxy)-5,5-dimethyl-2-cyclohexenone 2-(2'-Chlorophenyl)-3-(trifluoroacetoxy)-5,5-dimethyl-2-cyclohexenone 2-(2'-Chlorophenyl)-3-(acetoxy)-5,5-dimethyl-2-cyclohexenone 2-(2'-Trifluoromethyl-4'-nitrophenyl)-3-chlorocarbonyloxy-5,6-dimethyl-2-cyclohexenone 2-(2'-Methyl-4'-nitrophenyl)-3-chlorocarbonyloxy-5,6-dimethyl-2-cyclohexenone 2-(2'-Methyl-6'-nitrophenyl)-3-naphthylcarbonyloxy-4,4-diethyl-2-cyclohexenone 2-(2'-4'-Dimethylphenyl)-3-hexanoyloxy-5,5-dimethyl-2-cyclohexenone 2-(2',4'-Dimethylphenyl)-3-(2-ethylhexanoyloxy)-5,5-dimethyl-2-cyclohexenone 2-(2',3'-Dimethylphenyl)-3-stearoyloxy-5,5-dimethyl-2-cyclohexenone 2-(2',5'-Dichlorophenyl)-3-acetoxy-5,5-dimethyl-2-cyclohexenone 2-(2',4'-Dibromophenyl)-3-isobutyrloxy-5,5-dimethyl-2-cyclohexenone 2-(2',6'-Dichlorophenyl)-3-hexanoyloxy-5,5-dimethyl-2-cyclohexenone 2-(2',6'-Dichlorophenyl)-3-(2-ethylhexanoyloxy)-5,6-dimethyl-2-cyclohexenone 2-(2',5'-Dichlorophenyl)-3-stearoyloxy-5,5-dimethyl-2-cyclohexenone 2-(2',3'-Dimethylphenyl)-3-benzoyloxy-5,5-dimethyl-2-cyclohexenone 2-(2',4'-Dimethylphenyl)-3-phenylcarbonyloxy-4,6-dimethyl-2-cyclohexenone 2-(2',4'-Difluorophenyl)-3-(2',4'-dichlorophenylcarbonyloxy)-5,5-dimethyl-2-cyclohexenone 2-(2',4'-Dimethylphenyl)-3-(4'-dimethylaminophenylcarbonyloxy-5,5-dimethyl-2-cyclohexenone 2-(2',4'-Dimethylphenyl)-3-(4'-chlorophenylcarbonyloxy)-5,6-dimethyl-2-cyclohexenone 2-(2',4'-Dimethylphenyl)-3-(2'-ethylthiophenylcarbonyloxy)-5,5-dimethyl-2-cyclohexenone 2-(2',4'-Dimethylphenyl)-3-trifluoroacetoxy-5,5-dimethyl-2-cyclohexenone 2-(2',4'-Dimethylphenyl)-3-dimethylaminoacetoxy-4,5-dimethyl-2-cyclohexenone 2-(2',4'-Dimethylphenyl)-3-methylthioacetoxy-5,5-dimethyl-2-cyclohexenone 2-(2',4'-Dimethylphenyl)-3-methylsulfonylacetoxy-5,5-dimethyl-2-cyclohexenone 2-(2',4'-Dimethylphenyl)-3-(2-cyclohexenylcarbonyloxy)-5,5-dimethyl-2-cyclohexenone 2-(2'-Trichloromethyl-4'-nitrophenyl)-3-(2',4-dicyanohexanoyloxy)-4-(2'-chloroethyl)-2-cyclohexenone 2-(2'-Chloro-4'-nitrophenyl)-3-(2'-nitroethanoyloxy)-4,5-diethyl-2-cyclohexenone 2-(2'-Chloro-6'-methoxy-4'-nitrophenyl)-3-pentanoyloxy-6-(2'-cyanoethyl)-2-cyclohexenone 2-(2'-Chlorophenyl)-3-acetoxy-5,5-dimethyl-2-cyclohexone 2-(2'-Chlorophenyl)-3-(cyclopropylcarbonyloxy)-4,5-dimethyl-2-cyclohexenone 2-(2'-Bromophenyl)-3-(2-ethylhexanoyloxy)-5,6-dimethyl-2-cyclohexenone 2-(2',4',6'-Trimethylphenyl)-3-(4'-cyanobenzoyloxy)-4-methyl-2-cyclohexenone 2-(2'-Methylphenyl)-3-ethanoyloxy-5-(3'-ethylsulfinylphenyl)-2-cyclohexenone 2-(2'-Methylphenyl)-3-(4'-methoxyphenylcarbonyloxy)-5,5-dimethyl-2-cyclohexenone 2-(2',6'-Dimethylphenyl)-3-(2',4'-dicyanophenylcarbonyloxy)-5,5-dimethyl-2-cyclohexenone 2-(2',4'-Dimethylphenyl)-3-(3'-nitrophenylcarbonyloxy)-5,5-dimethyl-2-cyclohexenone 2-(2'-Methyl-4'-chlorophenyl)-3-(trifluoroacetoxy)-5,5-dimethyl-2-cyclohexenone 2-(2',4'-Dimethylphenyl)-3-(3'-methylthiobenzoyloxy)-5,5-dimethyl-2-cyclohexenone 2-(2'-Methylphenyl)-3-(2'-methylsulfinylbenzoyloxy)-5,5-dimethyl-2-cyclohexenone 2-(2'-Methylphenyl)-3-(4'-methylsulfonylphenylcarbonyloxy)-5,5-dimethyl-2-cyclohexenone 2-(2',4',6'-Trimethylphenyl)-3-cyclopropylcarbonyloxy-5,5-dimethyl-2-cyclohexenone 2-(2',4',6'-Trimethylphenyl)-3-(2-cyclohexenylcarbonyloxy)-5,5-dimethyl-2-cyclohexenone 2-(2'-Methylphenyl)-3-propynoyloxy-5,5-dimethyl-2-cyclohexenone 4-Acetoxy-3-(2',4'-dimethylphenyl)-bicyclo[3.2-1]oct-3-en-2-one 4-(2-Ethylhexanoyloxy)-3-(2'-chlorophenyl)-spiro[5.-5]unde-3-en-2-one 2-Hexanoyloxy-3-(2',4'-dichlorophenyl)-bicyclo[4.4.0]-dec-2-en-4-one 3-Isobutyryloxy-4-(4'-chlorophenyl)-2-(2',5'-dimethylphenyl)-2-cyclohexenone, and the like.

The dione esters employed in the insecticidal compositions of this invention can be prepared by one or more methods as indicated below in which R, R₁, R₂, R₃, R₄, R₅, R₆, R₇, Z, Z', Z'' and Z''' are as described above and X is hydrogen, hydroxyl or

except as noted. The term "lower alkyl" as employed in the claims means alkyl of up to 4 carbon atoms.

METHOD I

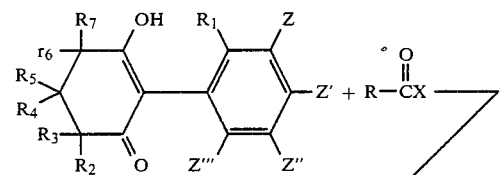

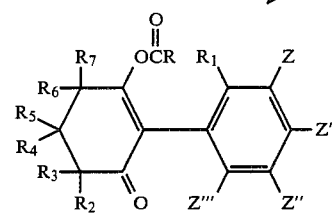

In the reaction illustrated in METHOD I, one equivalent of the corresponding 2-arylcyclohexane-1,3-dione compound is reacted with an appropriately substituted acid, acid halide or anhydride compound in the presence of at least one equivalent of an acid acceptor, preferably in an inert solvent.

The acid acceptor utilized in the reactions of METHOD I can be either an organic or an inorganic base. Illustrative of organic bases that are useful as acid acceptors in the conduct of these reactions one can mention, aromatic or heterocyclic tertiary amine compounds such as pyridine or N,N-dimethylaniline, linear tertiary amines, such as triethylamine, pyridine, trimethylamine or 1,4-diazobicyclo[2.2.2.]octane; or alkali metal alkoxides, as for example, sodium methoxide, sodium ethoxide or the like. Bases such as sodium carbonate, sodium hydroxide or potassium hydroxide are illustrative of inorganic bases that are useful as acid acceptors. Preferred organic acid acceptors are tertiary amines such as triethylamine, pyridine or trimethylamine.

In general, any organic solvent that is inert to the reactants or reaction conditions may be employed in the reaction of METHOD I. Illustrative of organic solvents which are generally suitable for use in the conduct of these reactions are saturated, unsaturated and aromatic hydrocarbons, e.g. hexane, cyclohexane, octane, cyclohexene, dodecane, naphtha, decalin, kerosene, cycloheptane, benzene, toluene, xylene, naphthalene or the like; ethers such as dioxane, tetrahydrofuran, diethyl ether, tetrahydropyran, 1,2-dimethoxybenzene, 1,2-diethyl benzene, the dialkyl ethers of ethylene glycol, of propylene glycol or chlorinated aliphatic hydrocarbons as for example, chloroform, dichloromethane, methylene dichloride, 1,1-dichloroethane, carbon tetrachloride or the like.

The 2-aryl-1, 3-cyclohexanedione compounds of this invention can be conveniently prepared by a variety of methods. Two preferred methods for preparing the compounds of this invention are illustrated by the reaction schemes set below in which $R_1$, $R_2$, $R_3$, $R_4$, $R_5$, $R_6$, $R_7$, Z, Z', Z" and Z'" are as described above and $R_{14}$ is alkyl except as noted:

METHOD II

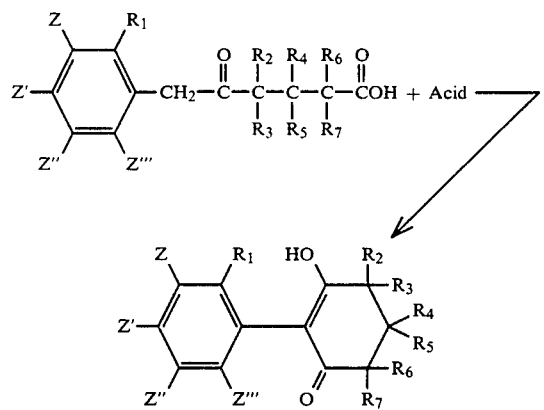

METHOD III

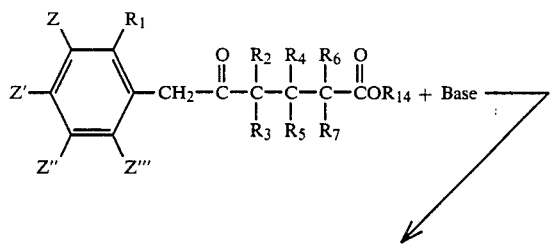

-continued
METHOD III

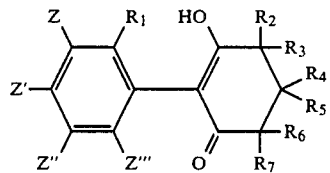

Preferably, the reactions illustrated in METHODS I and II are carried out by contacting equivalent amounts of the reactants in a suitable solvent. In the conduct of the reaction of METHOD II, types and quantities of the solvent employed are not critical. Illustrative of suitable inert solvents are ethanol, methanol, dimethylformamide, dimethylsulfoxide, methylene chloride, benzene, xylene, toluene, dioxane, dimethoxyethane, tetrahydrofuran and the like.

The reaction illustrated in METHOD I can be conducted in any solvent that is chemically inert to the reactants and to the reaction conditions, and in which the acid catalyst is soluble. Illustrative of such solvents are water and carboxylic acids, such as acetic acid, butanoic acid, or the like. The preferred reaction solvents are water and acetic acid.

The cyclization reaction illustrated in METHOD I is conducted in the presence of a strong mineral acid catalyst. Illustrative of mineral acids that are useful in the conduct of this reaction are sulfuric acid, hydrochloric acid, perchloric acid and the like. The preferred acid catalyst is sulfuric acid.

The quantity of acid catalyst employed in the conduct of the reaction of METHOD II is not critical. In general, to achieve a reasonable rate of reaction, the reaction is conducted in the presence of from about 1 to about 85 weight percent of the acid catalyst based on the total weight of the reaction solvent. Preferred acid concentrations are from about 50 to about 85 weight percent based on the weight of the reaction solvent.

The cyclization reaction illustrated in METHOD III is conducted in the presence of at least one equivalent of either a strong organic or a strong inorganic base. Illustrative of bases that are useful in the conduct of this reaction are the alkali metal alkoxides, as for example, sodium methoxide, sodium ethoxide or potassium tert-butoxide; the alkali metal alkylides; or the alkali metal hydrides such as sodium hydride, lithium hydride or the like. The preferred base in the conduct of this reaction is sodium hydride.

Alternative procedures for preparing a more limited class of 2-aryl-1, 3-cyclohexanedione compounds are illustrated by the general reaction schemes set forth below in which $R_1$, $R_2$, $R_3$, $R_4$, $R_5$, $R_6$, $R_7$, Z, Z', Z" and Z'" are as described above and X is fluorine or chlorine except as noted:

METHOD IV

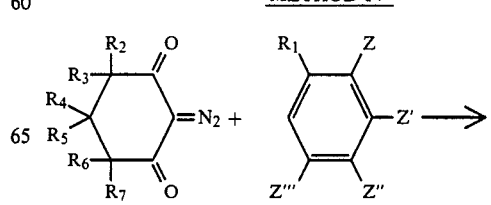

-continued
METHOD IV

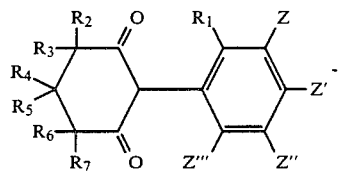

In METHOD IV, $R_1$ is alkyl and $Z$, $Z'$, $Z''$ and $Z'''$ are other than nitro.

METHOD V

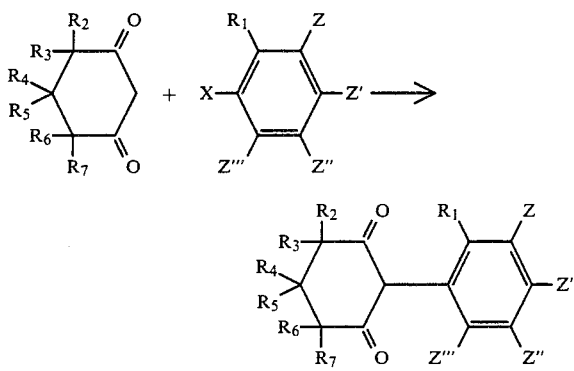

In Method V, $Z'$ is alkylsulfonyl or nitro; or $Z'$ may also be alkyl or alkoxy when either $R_1$ or $Z'''$ is nitro.

The procedure illustrated in METHOD IV involves the photosensitized decomposition of a 2-diazocycloalkane-1, 3-dione compound in an aromatic solvent, in the presence of a photosensitizer, preferably benzophenone. In this procedure an appropriately substituted 2-diazocycloalkane-1, 3-dione compound is photochemically decomposed to form the corresponding triplet carbene which, in turn, reacts with a suitable aromatic solvent to form the desired 2-arylcycloalkane-1, 3-dione compound. The photolysis reaction is carried out using ultraviolet radiaton having a wavelength of greater than 290 nanometers. The ultraviolet radiation can be obtained from any conventional ultraviolet radiation source known to those skilled in the photolysis art. Illustrative of suitable sources for generating ultraviolet radiation are high and low pressure mercury arc lamps, germacidal lamps, "black" lights and the like.

Preferably the reaction illustrated in METHOD V is carried out by contacting equivalent amounts of the reactants in an appropriate solvent, in the presence of at least an equivalent of either an organic or an inorganic base. Illustrative of suitable reaction solvents, are dimethylformamide, dimethylsulfoxide, hexamethylphosphoramide and the like. Illustrative of bases that may be utilized in the conduct of this reaction are alkali metal carbonates or bicarbonates, as for example, sodium bicarbonate or potassium carbonate; alkali metal hydrides, such as lithium hydride, sodium hydride or potassium hydride, or alkali metal alkoxides or hydroxides, such as sodium hydroxide, sodium methoxide or potassium tert-butoxide. The preferred base is anhydrous potassium carbonate.

The reactions of METHODS I to V are neither temperature nor pressure sensitive and may be conducted over a broad temperature and pressure range to yield the desired product. In general, these reactions can be conducted at a temperature of from about $-30°$ C. to about $200°$ C. For convenience these reactions are conducted at autogeneous or atmospheric pressure.

The alkali metal and ammonium salts of the compounds of this invention can be conveniently prepared in accordance with conventional methods. For example, the alkali metal and ammonium salts can be prepared by treating the corresponding 2-aryl-1, 3-cyclohexanedione compound with an alkali metal alkoxide, or ammonia, or an amine respectively.

The 6-aryl-5-ketopolyalkylhexanoic acid compounds utilized as reactants in the reaction illustrated in METHOD I can be conveniently prepared by reacting an appropriately polysubstituted benzyl cyanide compound with a suitable polyalkyl glutaric acid derivative in the presence of base to form the corresponding 6-aryl-6-cyano-5-ketopolyalkylhexanoic acid ester compound which, in turn, is hydrolyzed under acidic conditions to the desired reactant.

The 6-aryl-5-ketopolyalkylhexanoic acid ester compounds utilized as reactants in the reaction illustrated in METHOD II can be conveniently prepared by esterifying the 6-aryl-5-ketopolyalkylhexanoic acid reactant of METHOD I via conventional esterification techniques.

The 2-diazo-1, 3-cyclohexanedione compounds utilized as reactants in the reaction of METHOD III can be prepared by treating an appropriately substituted cyclohexanedione-1, 3-dione compound with a sulfonyl azide in the presence of an acid acceptor, as for example, a trialkylamine, as described in more detail in H. Stetter and K. Kiehr, *Chem. Ber.*, 98 1181 (1965), M. Regitz and P. Stodler, *Liebigs Ann. Chem.*; 687, 214 (1967) and references cited therein. The cyclohexane-1, 3-dione compound, in turn, can be prepared by conventional methods, as for example by condensing an appropriately substituted $\alpha\beta$-unsaturated ketone with diethyl malonate in the presence of a base catalyst as described in more detail in K. W. Rosenmund, H. Herzberg and H. Scutt, *Chem. Ber.*, 87, 1258 (1954), C. K. Shuang and Y. L. Tien, *Chem. Ber.*, 69, 27 (1936) and references cited therein.

The substituted aryl, cyclohexanedione, acid halide, acid and anhydride compounds employed as reactants in the reactions illustrated in METHOD I and V are known classes of compounds that can be either obtained from commercial sources or prepared in accordance with conventional methods known to those skilled in the synthetic arts.

As hereinbefore indicated, the dione esters are used as synergist with the known pyrethroid, carbamate or organophosphate insecticides. These insecticides can be represented by the following formulae:
wherein $R_8$ is

(II)

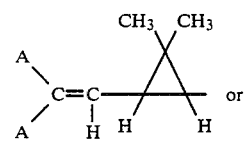

or

-continued

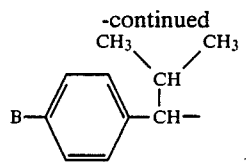

wherein H is Cl or Br, and
wherein B is Cl, OCHF$_2$ or OCF$_3$ and

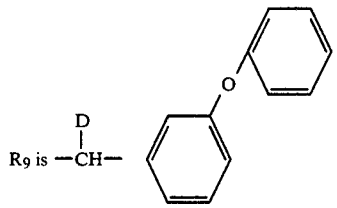

wherein D is H—C≡CH or —C≡N;

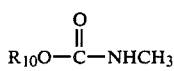     (III)

wherein R$_{10}$ is 1-naphthyl, 2,2-dimethylbenzofuran-7-yl, 3,4,5-trimethylphenyl, 4-(methylthio)3,5-xylyl or 2,2-dimethyl-1,3-benzodioxol-4-yl; or

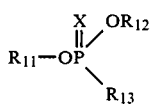     (IV)

wherein X is O or S; R$_{11}$ is aryl or substituted aryl where the substituents may be one or more groups selected from nitro, chloro, bromo, alkylthio, alkylsulfinyl, alkyl or alkylsulfonyl; R$_{12}$ is lower alkyl R$_{13}$ is alkyl, aryl, or alkylthio.

Hence, the insecticides employed with the diones are the pyrethroid insecticides such as permethrin, decamethrin, fenvalerate and the like; carbamate insecticides such as carbaryl, methomyl, thiodicarb and the like and organophosphate insecticides such as methyl parathion sulprophos and the like.

Illustrative insectides which can be employed with the dione esters include, among others, 3-phenoxybenzyl 2-(2,2-dichlorovinyl)-3,3-dimethylcyclopropanecarboxylate, 3-phenoxybenzyl 2-(2,2-dibromovinyl)-3,3-dimethylcyclopropanecarboxylate, 3-phenoxybenzyl 2-(2,2-dichlorovinyl)-3,3-dimethylcyclopropanedicarboxylate, α-cyano-3-phenoxybenzyl α-isopropyl-4-chlorophenylacetate, 1-naphthyl N-methylcarbamate, O,O-dimethyl-O-p-nitrophenylphosphorothionate, O-ethyl-O-[4(methylthio)phenyl]S-propyl phosphorodithioate, and the like.

In practice, the ester diones are employed with the other insecticides in a synergistically effective amount. By the term "synergistically effective amount" is meant the amount of ester dione which when used with the other insecticide results in a mixture which has a greater effect on insects than the sum total of each of the components thereof when used alone. In practice, the weight ratio of the dione esters of this invention to the pesticide vary widely with each pesticide and with each insect to be controlled. However, in general, the weight ratio of dione ester to pesticide will be in the range of 500:1 and 1:1 but is preferably in the range of 100:1 to 10:1.

The following examples are illustrative of the best mode presently contemplated for the practice of the invention:

EXAMPLE I

Preparation of
2-(2'-Chloro-4'-Nitrophenyl)-5,5-dimethyl-1,3-cyclohexanedione

A solution containing 42.05 g (0.300 mol) of 5,5-dimethyl-1,3-cyclohexanedione and 100 g (0.718 g-atom) of anhydrous potassium carbonate in 300 ml of dry dimethylformamide was heated to 75° C. under nitrogen and stirred for one hour. The 3,4-dichloronitrobenzene, 57.60 g (0.300 mol) was dissolved in 100 ml dimethylformamide and added dropwise to the reaction mixture while stirring and maintaining the temperature of the reaction mixture at 75° C. A deep red-colored solution formed, and when the addition was complete the reaction temperature was raised to 100° C. and held at this temperature for 3 hours. Most of the dimethylformamide was removed by vacuum distillation. The residue was poured into 2l of ice water and extracted three times with 500 ml of benzene. Nitrogen was then passed through the aqueous solution while warming to remove dissolved benzene. The aqueous solution was cooled in an ice bath and acidified to give a tacky precipitate, which, upon warming solidified and was collected by suction filtration. The product was recrystallized from acetone to give 31.7 g (36%) or 2-(2'-Chloro-4'-nitrophenyl)-5,5-dimethyl-1,3-cyclohexandione as a white powder, m.p. 250°–253° C.

Calculated for C$_{14}$H$_{14}$ClNO$_4$.1/2H$_2$O: C. 55.18; H, 4.96; N, 4.60. Found: C, 55.53; H, 4.73; N, 5.09.

EXAMPLE II

Preparation of
2-(2'-Chloro-4'-aminophenyl)-5,5-dimethyl-1,3-cyclohexanedione

A solution of 20.0 g (0.067 mol) of 2-(2'-chloro-4'-nitrophenyl)-5,5-dimethyl-1,3-cyclohexanedione in 150 ml of concentrated ammonium hydroxide and 150 ml of ethanol was stirred at room temperature while passing hydrogen sulfide gas through the solution at such a rate that all of the H$_2$S was absorbed. When the solution was saturated with H$_2$S, the temperature was raised to the reflux point and H$_2$S continuously passed slowly through the refluxing solution for 24 hours. The reaction mixture was filtered to remove sulfur, and the filtrate evaporated under reduced pressure. To the residue was added 300 ml of 0.25N NaOH, and the solution filtered once more. The filtrate was cooled and carefully acidified to pH=4 with 6N HCl. 2-(2'-Chloro-4'-aminophenyl)-5,5-dimethyl-1,3-cyclohexanedione was collected by suction filtration.

Yield: 13.3 g (74%), m.p. 218°–219° C.

Calculated for C$_{14}$H$_{16}$Cl NO$_2$.1/2H$_2$O. C, 61.20; H, 6.24; N, 5.10. Found: C, 60.44; H, 5.83; N, 5.32.

EXAMPLE III

Preparation of 2-(2'-Chlorophenyl)-5,5-dimethyl-1,3-cyclohexanedione 2-(2'-Chloro-4'-aminophenyl)-5,5-dimethyl-1,3-cyclohexanedione (9.66 g. 0.0364 mol) was added to 7.0 ml of water, and the mixture stirred and heated almost to boiling. An additional 15.0 ml of HCl was added and the mixture cooled to 0°–5° C. A solution of 3.22 g (0.0467 mol) of sodium nitrate in 9.0 ml of water was added dropwise while the reaction mixture was stirred and maintained at 0°–5° C. When the addition of the sodium nitrite solution was complete, the reaction mixture was stirred at 0°–5° C. for one hour.

The diazonium salt solution prepared above was added in portions to 161 ml of 50% hypophosphorous acid at 0° C., with stirring and cooling. The reaction mixture was stirred for 12 hours and filtered to give 8.55 g of a tan solid. This material was chromatographed through 250 g of silica gel (0.063–0.2 mm) eluting with a gradient from pure benzene to 70:30 benzene-ethyl acetate. A total of 7.12 g of reaction product was obtained from the chromatography and recrystallized from benzene-ethyl acetate to give 6.85 g (75%) of 2-(2'-Chorophenyl)-5,5-dimethyl-1,3-cyclohexanedione as white crystals. m.p. 191°–192° C.

Calculated for $C_{14}H_{15}C_1O_2$: C, 67.07; H, 6.03. Found: C, 67.04; H, 6.00.

EXAMPLE IV

Preparation of 2-(2',4'-Dichlorophenyl)-5,5-dimethyl-1,3-cyclohexanedione

A fresh sample of cuprous chloride was prepared by slowly adding a solution of 2.09 g of sodium bisulfite and 1.38 g of NaOH in 20 ml of water to a solution of 9.86 g $CuSO_4.5H_2O$ and 2.75 g NaCl in 100 ml of hot water. The suspension of CuCl was cooled to room temperature, and washed several times with water while exercising care to avoid exposure of the cuprous chloride to air.

A suspension of 5.00 g (0.0188 mol) of 2-(2'-chloro-4'-aminophenyl)-5,5-dimethyl-1,3-cyclohexanedione in 75 ml of water containing 4.0 ml of concentrated HCl was stirred and heated almost to boiling for 10 min., then cooled to 10° C. and an additional 7 ml of conc. HCl added and the solution cooled to 0°–5° C. A solution of 2.00 g (0.0282 mol) of sodium nitrite in 6.0 ml of water was added dropwise to the amine hydrochloride solution while maintaining the temperature at 0°–5° C. When all the $NaNO_2$ solution had been added, the diazonium salt solution was stirred for 30 min. at 0° C.

The diazonium salt solution was added, in small portions to a solution of the cuprous chloride in 40 ml of conc. HCl at 0° C. When all of the diazonium salt solution had been added, the reaction mixture was stirred overnight at room temperature and filtered to give 6.22 g of a tan solid, m.p. 175°–178° C. This crude product was chromatographed through silica gel (0.063–0.2 mm) using a benzene-ethyl acetate gradient from pure benzene to 70:30 benzene-ethyl acetate to give 3.51 g (65%) of 2-(2',4'-Dichlorophenyl-5,5-dimethyl-1,3-cyclohexanedione as a white, crystalline solid, m.p. 208.5°–210° C.

Calculated for: $C_{14}H_{14}Cl_2O_2$: C, 58.97; H, 4.95. Found: C, 59.06; H, 4.82.

EXAMPLE V

Preparation of 2-(2',6'-Dichloro-4'-nitrophenyl)-5,5-dimethyl-1,3-cyclohexanedione A solution of 30.98 g (0.221 mol) of 5,5-dimethyl-1,3-cyclohexanedione and 76.36 g (0.553 mol) of anhydrous potassium carbonate in 300 ml of dimethylformamide was heated to 75° C. with stirring under $N_2$ for one hour. The 3,4,5-trichloronitrobenzene (50.0 g, 0.221 mol) was dissolved in 100 ml of dimethylformamide and added to the reaction mixture, while stirring and maintaining the temperature at 75° C. A deep red-colored solution was formed, and when the addition was complete the temperature was raised to 100° C. and the mixture stirred over night at this temperature. Most of the dimethylformamide was removed by vacuum distillation, and 21 of water was added to the residue. The aqueous solution was extracted three times with 500 ml portions of benzene, then $N_2$ was passed through the aqueous solution while warming to remove dissolved benzene. The solution was cooled in an ice bath and acidified with 6N HCl to give 63.8 g (87%) of 2-(2',6'-dichloro-4'-nitrophenyl)-5,5-dimethyl-1,3-cyclohexanedione as a tan powder, m.p. 288°–290° C.

Calculated for $C_{14}H_{13}Cl_2NO_4$: C, 50.93; H, 3.97; N, 4.24. Found: C, 50.09; H, 3.79; N, 4.26.

EXAMPLE VI

Preparation of 2-(2',6'-Dichloro-4'-aminophenyl)-5,5-dimethyl-1,3-cyclohexanedione A solution of 20.0 g (0.0606 mol) of 2-(2',6'-dichloro-4'-nitrophenyl)-5,5-dimethyl-1,3-cyclohexanedione in 150 ml conc. $NH_4OH$ and 150 ml of ethanol was stirred at room temperature while passing $H_2S$ gas through the solution at such a rate that all of the $H_2S$ was absorbed. After the solution was saturated with $H_2S$, it was refluxed 24 hours while continuously passing $H_2S$ slowly through the solution. The reaction mixture was cooled to room temperature, the precipitated sulfur removed by filtration, and the filtrate evaporated to dryness under reduced pressure. To the residue was added 300 ml of 0.25N NaOH, and the solution filtered once more. The filtrate was cooled and acidified to pH=4 with 6N HCl. A tan solid formed which was collected by filtration to give 11.2 g when dry. This material was washed with methylene chloride to give 8.2 g (45%) of 2-(2',6'-dichloro-4'-aminophenyl)-5,5-dimethyl-1,3-cyclohexanedione as a white powder, m.p. 243° d.

Calculated for $C_{14}H_{15}C_{12}NO_2$: C, 56.02; H, 5.04; N, 4.67. Found: C, 56,34; H, 4.95; N, 4.67.

EXAMPLE VII

Preparation of 2-(2',6'-Dichlorophenyl)-5,5-dimethyl-1,3-cyclohexanedione

The 2-(2',6'-dichloro-4'-aminophenyl)-5,5-dimethyl-1,3-cyclohexanedione (5.00 g, 0.0167 mol) was added to 3.5 ml of concentrated HCl in 75 ml of water, and the mixture stirred and heated almost to boiling. The suspension was cooled to 10° C. and an additional 7.5 ml of conc. HCl was added. The mixture was cooled to 0°–5° C. and a solution of 1.44 g (0.0209 mol) of sodium nitrite in 3.5 ml. of water was added dropwise while the reaction mixture was stirred and maintained at 0°–5° C. When addition of the sodium nitrite solution was complete, the reaction mixture was stirred at 0° C. for one hour.

The diazonium salt solution prepared above was added in portions to 75 ml of 50% hypophosphorous acid at 0° C. with stirring and cooling. The reaction mixture was stirred for 2 hours and filtered to give 5.03 g of brown powder. This material was recrystallized from benzene-chloroform to give 2.69 g of a light tan solid m.p. 227°–229° C. The residue from the mother liquor (1.70 g) was chromatographed through silica gel (0.063–0.2 mm) to give 0.84 g of a white solid, m.p. 228°–232° C. Total yield of 2-(2′,6′-Dichlorophenyl)-5,5-dimethyl-1,3-cyclohexane-1,3-dione was 3.53 g (74%).

Calculated for: $C_{14}H_{14}Cl_2O_2$: C, 58.97; H, 4.95 Found: C, 58.64; H, 4.86.

EXAMPLE VIII

Preparation of 2-(2′,4′,6′-Trimethylphenyl)-cyclohexane-1,3-dione

A solution of 5.00 g (0.036 mol) of 2-diazocyclohexane-1,3-dione in 500 ml of mesitylene (dry, distilled) containing 32.8 g (0.18 mol) benzophenone was degassed with nitrogen for one hour and irradiated with a 200 watt mercury arc lamp fitted with a borosilicate glass filter until the complete disappearance of the diazo band (4.68 u) in the infrared was observed. The reaction was also monitored by thin layer chromatography (90:10 ethyl acetate-benzene) and irradiation continued until no diazoketone at $R_f=0.31$ could be seen. The irradiation required 11 hours. The mesitylene was extracted with 0.25N sodium hydroxide until a small aliquot showed no cloudiness upon acidification. The combined base extracts were washed twice with 200 ml portions of ether, and acidified (pH 3–5) with 1N HCl. The aqueous solution was extracted three times with 75 ml portions of chloroform, dried over anhydrous MgSO$_4$, and the solvent stripped to give 5.06 g of a tan solid.

This solid was chromatographed through 250 g silica gel (0.063–0.2 mm) eluting with a gradient from pure benzene to 80:20 benzene-ethyl acetate. A total of 2.60 g (31%) of a white solid (homogeneous by thin layer chromatography) was obtained and recrystallized from diisopropyl ether to give 1.96 g of 2-(2′,4′,6′-Trimethylphenyl)cyclohexane-1,3-dione as white crystals, mp 196°–198° C.

Calculated for: $C_{15}H_{18}O_2$: C, 78.23; H, 7.88 Found: C, 77.94; H, 8.20.

EXAMPLES IX AND X

Preparation of 2-(2′,4′-Dimethylphenyl)-5,5-dimethylcyclohexane-1,3-dione and 2-(2′,6′-dimethylphenyl)-5,5-dimethylcyclohexane-1,3-dione A solution of 5.00 g (0.0301 mol.) of 2-diazo-5,5-dimethylcyclohexane-1,3-dione in 500 ml of m-xylene containing 27.4 g (0.15 mol) of benzophenone was degassed with nitrogen for one hour and irradiated overnight with a 200 watt mercury arc lamp fitted with a borosilicate glass filter. The photolysis mixture was extracted with 0.25N NaOH, the combined base extracts washed with ether and acidified with chloroform, dried over anhydrous mgSO$_4$ and the solvent removed to leave 3.61 g of a tan solid. Irradiation was repeated using 7.00 g (0.042 mol) of 2-diazo-5,5-dimethylcyclohexane-1,3-dione and 38.38 g (0.21 mol) of benzophenone in 500 ml of m-xylene. Workup gave 5.48 g of tan solid.

The combined crude products (9.09 g) were chromatographed through silica gel (0.063–0.2 mm) using benzene-ethyl acetate as eluent. The column was eluted with (1) 500 ml benzene (2) 500 ml of 95.5 benzene-ethyl acetate (3) 1000 ml of 90:10 benzene-ethyl acetate and (4) 1000 ml of 80:20 benzene-ethyl acetate. After collecting 2 liters of solvent, the column was attached to an automatic fraction collector and 15 ml fractions collected. Tubes 1–94 contained small amounts of a yellow oil. Tubes 95–150 contained a light yellow solid which showed one component ($R_f$ 0.55 in 50:50 hexane-ethyl acetate) by thin layer chromatography and weighed 2.18 g. This material was recrystallized from benzene to give 1.17 g of 2-(2′,4′-Dimethylphenyl)-5,5-dimethyl-1,3-cyclohexanedione as a white powder, mp 167°–169° C.

Calculated for: $C_{16}H_{20}O_2$: C, 78.65; H, 8.25. Found: C, 78.68; H, 8.12.

This compound was shown to be 2-(2′,4′-dimethylphenyl)-5,5-dimethyl-1,3-cyclohexanedione.

Tubes 151–230 were combined to give 2.0 g of white solid showing one component ($R_f$ 0.57 in 50:50 hexane-ethyl acetate by thin layer chromatography. This material was recrystallized from benzene to give 1.90 g of 2-(2′,6′-Dimethylphenyl)-5,5-dimethyl-1,3-cyclohexanedione as white crystals, mp 177°–186° C.

Calculated for: $C_{16}H_{20}O_2$: C, 78.65; H, 8.25. Found: C, 78.28; H, 8.21.

This compound was shown to be 2-(2′, 6′-Dimethylphenyl)-5,5-dimethyl-1,3-cyclohexanedione.

EXAMPLE XI

Preparation of 2-Diazo-5-phenylcyclohexane-1,3-dione

A solution of 20.0 g (0.106 mol) of 5-phenylcyclohexane-1,3-dione in 75 ml ethanol was cooled to −10° C. and stirred magnetically under nitrogen. To the mixture was added 10.75 g (0.106 mol) of triethylamine. The tosyl azide (20.95 g 0.106 mol) was added all at once, and the mixture stirred for one hour at 0°–5° C. The solvent was removed under vacuum at a temperature less than 40° C. To the residue was added 200 ml ether, and the mixture extracted with a solution containing 3.1 g potassium hydroxide in 200 ml of water. The ethereal solution was dried over anhydrous MgSO$_4$ filtered and the solvent removed to give a yellow solid which was recrystallized from ethanol-hexane to give 8.38 g (32%) of 2-diazo-5-phenylcyclohexane-1,3-dione as yellow crystals, mp 122°–124° C.

EXAMPLE XII

Preparation of 2-(2′,4′,6′-Trimethylphenyl)-5-phenylcyclohexane-1,3-dione

A solution of 7.0 g (0.0327 mol) of 2-diazo-5-phenylcyclohexane-1,3-dione and 29.77 g (0.163 mol) of benzophenone in 500 ml of mesitylene was degassed for one hour with nitrogen and irradiated with a 200 watt mercury arc lamp fitted with a borosilicate glass filter overnight. The photolysis mixture was extracted with 0.25N sodium hydroxide, the combined base extracts washed with ether, acidified with 1N HCl, and extracted with chloroform. The chloroform solution was dried over anhydrous MgSO$_4$, and the solvent stripped to give 5.7 g of tan solid. This material was purified by column chromatography on silica gel (0.063–0.2 mm) using benzene-ethyl acetate to give 5.7 g (57%) of a white solid. This was recrystallized from benzene-ethyl acetate to give 4.08 g (41%) of 2-(2',4',6'-Trimethylphenyl)-5-phenylcyclohexane-1,3-dione as a white crystalline solid, mp. 215°–216° C.

Calculated for: $C_{21}H_{22}O_2$: C, 82.32; H, 7.24. Found: C, 82.38; H, 7.14.

EXAMPLE XIII

Preparation of 2-(2',6'-Dimethyl-4'-t-butylphenyl)-5,5-dimethyl-1,3-cyclohexanedione A solution of 7.00 g (0.042 mol) of 2-diazo-5,5-dimethylcyclohexane-1,3-dione in 300 ml of 5-t-butyl-m-xylene and 250 ml chlorobenzene containing 38.38 g (0.21 mol) of benzophenone was irradiated overnight with a 200 watt mercury arc lamp fitted with a borosilicate glass filter after degassing for 1 hour under nitrogen. The photolysis mixture was extracted with 0.25N NaOH, washed with ether, acidified with 1N HCl, and extracted with chloroform. The chloroform was dried over anhydrous $MgSO_4$ and stripped to give a crude yellow solid. The photolysis was repeated and the combined crude product from these reactions was chromatographed through silica gel (0.063–0.2 mm) using benzene-ethyl acetate. The solid obtained from the chromatography was recrystallized from benzene to give 2.76 g (11%) of 2-(2',6'-dimethyl-4'-t-butylphenyl)-5,5-dimethyl-1,3-cyclohexanedione as white crystals, mp 244°–49° C.

Calculated for: $C_{20}H_{28}O_2$: C, 79.95; H, 9.39. Found: C, 79.76; H, 9.45.

EXAMPLE XIV

Preparation of 2-Diazodecalin-1,3-dione

A solution of 10.0 g (0.0768 mol) of decalin-1,3-dione in 50 ml of ethanol was magnetically stirred under nitrogen and cooled to −10° C. To the solution was added 7.77 g (0.0768 mol) of triethylamine followed by 15.14 g (0.0768 mol) of p-toluenesulfonylazide added all at once. The mixture was stirred for one hour at 0° C., and the solvent removed at reduced pressure at a temperature of less than 40° C. To the residue was added 200 ml of ether, and the ether removed to yield a yellow solid. This was recrystallized from ethanol to give 5.23 g of yellow crystals, mp 81°–83° C.

EXAMPLE XV

Preparation of 2-(2'-Methylphenyl)-decalin-1,3-dione

A solution of 7.0 g (0.0364 mol) of 2-diazodecalin-1,3-dione and 33.18 g (0.182 mol) of benzophenone in 500 ml of toluene was degassed for one hour with nitrogen and irradiated with a 200 watt mercury arc lamp fitted with a borosilicate glass filter overnight. The photolysis mixture was extracted with 0.25N NaOH, the combined base extracts washed with ether, acidified with 1M HCl and extracted with chloroform. The chloroform extracts were dried over anhydrous $MgSO_4$, and the solvent removed to give 4.56 g of a yellow crude product. This was purified by column chromatography through silica gel (0.063–0.2 mm) with benzene-ethyl acetate. The solid obtained was recrystallized from benzene to give 1.85 g (20%) of 2-(2'-Methylphenyl)-decalin-1,3-dione as white crystals, mp 165°–167° C.

Calculated for: $C_{17}H_{20}O_2$: C, 79.65; H, 7.86. Found: C, 79.82; H, 7.43.

EXAMPLE XVI

Preparation of Ethyl 6-(2',4'-Dimethylphenyl)-6-cyano-5-keto-3,3-dimethylhexanoate A clean, dry 500 ml 3-neck flask was equipped with a reflux condenser, mechanical stirrer, addition funnel and nitrogen inlet. The flask was charged with 70 ml of absolute ethanol followed by 6.00 g (0.26 g-atom) of sodium, and the reaction mixture stirred and heated until all the sodium had dissolved. The temperature of the reaction mixture was then raised to the reflux point, and a mixture of 29.04 g (0.20 mol) of 2,4-dimethylbenzyl cyanide and 64.88 g (0.30 mol) of diethyl 3,3-dimethyl glutarate added, dropwise, over a 2 hour period through the addition funnel. When the addition was complete, the reaction mixture was maintained at reflux for 12 hrs. At the end of this time, approximately ⅔ of the ethanol was distilled off, and the reaction mixture refluxed for 2 hrs. more, then cooled to room temperature and poured into 600 ml of an ice water mixture.

The basic aqueous solution was extracted twice with 300 ml of ether, and then acidified (pH=3) with 6N HCl. An oil formed, and the aqueous acid solution was extracted twice with 250 ml portions of ether. The ether phase from the extraction of the aqueous acid was washed twice with water, dried over anhydrous $MgSO_4$, and stripped to leave 52.83 g (84%) of ethyl 6-(2',4'-Dimethylphenyl)-6-cyano-5-keto-3,3-dimethylhexanoate as a clear, colorless, very viscous oil. This oil was not purified, but was characterized by infrared and nuclear magnetic resonance spectrometry.

IR (neat, μ, principal absorptions): 2.8–3.2 (OH, enol); 4.55 (C≡N); 5.85, 6.02, 6.19 (C=O); 6.3 (C=C); 7.45, 8.25, 9.85, 12.25.

NMR ($CDCl_3$, δ): 1.20 (multiplet, 9H); 2.33 (multiplet, 8H); 2.68 (multiplet, 2H); 4.17 (quartet, 2H): 4.90 and 12.0 (singlet, 1H); 7.05 (multiplet, 3H).

EXAMPLE XVII

Preparation of 2-(2',4'-Dimethylphenyl)-5,5-dimethyl-1,3-cyclohexanedione and 6-(2',4'-Dimethylphenyl)-5-keto-3,3-dimethylhexanoic acid A one-neck round bottom flask was charged with 52.50 g (0.17 mol) of ethyl 6-(2',4'-dimethylphenyl)-6-cyano-3,3-dimethylhexanoate, 250 ml of concentrated hydrochloric acid, 250 ml of glacial acetic acid, and 100 ml of water. The reaction mixture was stirred and refluxed for 48 hours. After 12 hours and 24 hrs. of refluxing, an additional 100 ml of conc. HCl and 100 ml glacial HOAC were added. After 48 hours, the mixture was stripped to dryness under reduced pressure. To the residue were added 150 ml of water and 150 ml of ethyl ether, and the mixture shaken vigorously. A white, crystalline precipitate formed, and this was removed by suction filtration to give 13.20 g (32%) of 2-(2',4'-Dimethylphenyl)-5,5-dimethyl-1,3-cyclohexanedione as a white, crystalline solid, m.p. 167°–168.5° C.

Calcd. for $C_{16}H_{20}O_2$: C, 78.65; H, 8.25. Found: C, 78.68; H, 8.12.

The ether layer was separated from the filtrate, washed once with water, dried over anhydrous $MgSO_4$ and stripped to give 29.04 g (65%) of 6-(2',4'-dimethylphenyl)-5-keto-3,3-dimethylhexanoic acid as a viscous yellow oil. This oil was not purified, but was characterized by infrared and nuclear magnetic resonance spectrometry.

IR (CHCl$_3$,μ principal absorptions): 2.9–4.3 (OH); 5.90 (C=O).

NMR (CDCl$_3$,δ): 1.10 (singlet, 6H); 2.20 singlet, 3H; 2.30 (singlet, 3H); 2.50 (singlet, 2H); 2.62 (singlet, 2H); 3.70 (singlet, 2H); 7.08 (singlet, broad, 3H).

EXAMPLE XVIII

Preparation of 2-(2'-Chlorophenyl)-1,3-cyclohexanedione

A 500 ml round bottom flask was charged with 10.0 g (0.0416 mol) of 6-(2'-chlorophenyl)-5-ketohexanoic acid and 100 ml of 72% sulfuric acid. The reaction mixture was stirred and heated to 120° C. for 5½ hours (oil bath), then poured into 600 ml of an ice water mixture. A tacky, white solid formed, and this was extracted into 300 ml of methylene chloride. The CH$_2$Cl$_2$ solution was washed six times with water, dried over anhydrous MgSO$_4$ and stripped to leave 8.87 g of a tacky, white solid. This material was recrystallized from ethyl acetate to give 5.85 g (63%) of 2-(2'-chlorophenyl)-1,3-cyclohexanedione as a white, crystalline solid, m.p. 148.5°–149° C.

Calculated for: C$_{12}$H$_{11}$ClO$_2$: C, 64.73; H, 4.98. Found: C, 64.49; H, 4.89.

EXAMPLE XIX

Preparation of 6-(2',4'-Dimethylphenyl)-5-ketohexanoic acid

Utilizing the procedure of EXAMPLE XVII ethyl 6-(2',4'-dimethylphenyl)-6-cyano-5-ketohexanoate was hydrolyzed in the presence of concentrated hydrochloric acid to prepare 6-(2',4'-dimethylphenyl)-5-ketohexanoic acid in 49% yield as a tan solid, m.p. 75.0°–76.5° C. This solid was characterized by infrared and nuclear magnetic resonance spectrometry.

IR (CHCl$_3$,μ principal absorptions): 2.9–4.2 (OH); 5.92 (C=O).

NMR (CDCl$_3$, δ): 1.7–3.3 (multiplet, 6H); 2.48 (singlet 3H); 3.71 (singlet, 2H); 7.31 (singlet, broad, 3H).

EXAMPLE XX

Preparation of Ethyl 6-(2',4'-Dimethylphenyl)-5-ketohexanoate

A 500 ml one-neck round bottom flask equipped with a Soxhlet extraction apparatus containing 100 g of molecular sieves having a pore size of 3 A was charged with 12.74 g (0.0544 mol) of 6-(2',4'-dimethylphenyl)-5-ketohexanoic acid, 125 ml of absolute ethanol, 125 ml of dry benzene, and 2.0 ml of concentrated sulfuric acid. The mixture was refluxed for 12 hours, then ⅔ of the ethanolbenzene removed under reduced pressure. The residue was poured into 500 ml of ice water, and extracted into 300 ml of ether. The ether was washed three times with 10% K$_2$CO$_3$, then once with water, dried over anhydrous MgSO$_4$, and removed to leave 13.34 g of a dark yellow oil. This was distilled to give 12.77 g (89%) of ethyl 6-(2',4'-Dimethylphenyl)-5-ketohexanoate as a clear, colorless oil, b.p. 133°–145° C. (0.05 mm). This oil was further characterized by infrared and nuclear magnetic resonance spectrometry.

IR (neat, μ, principal absorptions): 5.85 (C=O), 8.60 (C=O)

NMR (CDCl$_3$, δ): 1.15 (triplet, 3H); 1.50–2.6 (multiplet, 6H); 2.10 (singlet, 3H); 2.20 (singlet, 3H; 3.52 (singlet, 2H); 3.95 (quartet, 2H); 6.80 (singlet, broad, 3H).

EXAMPLE XXI

Preparation of 2-(2',4'-Dimethylphenyl)-1,3-cyclohexanedione

A 500 ml 3-neck round bottom flask was equipped with a mechanical stirrer, addition funnel, and reflux condenser. The glassware was dried thoroughly and the flask charged with 4.62 g (0.096 g-atoms) of 50% sodium hydride in mineral oil. The oil was washed off the NaH using toluene, and then 100 ml of toluene added. The mixture was warmed to 65° C. and 12.62 g (0.0481 mol) of ethyl 6-(2',4'-dimethylphenyl)-5-ketohexanoate added, dropwise, over a 2 hr. period. The mixture was maintained at 65° C. for 12 hrs., then carefully quenched with 25 ml of ice water. The reaction mixture was diluted with 250 ml of water and extracted twice with 150 ml of ether. The aqueous base solution was acidified to pH=3 with 6N HCl, and extracted twice with 150 ml of methylene chloride. The methylene chloride was washed with water, dried over anhydrous MgSO$_4$, and stripped to give 5.88 g of a semisolid. This was recrystallized from ethyl acetate to give 5.10 g (49%) of 2-(2',4'-Dimethylphenyl)-1,3-cyclohexanedione as a white, crystalline solid, m.p. 143°–145° C.

Calculated for: C$_{14}$H$_{16}$O$_2$: C, 77.75; H, 7.46. Found: C, 76,99; H, 7.46.

EXAMPLE XXII

Preparation of Ethyl 6-(2',5'-Dimethylphenyl)-6-cyano-5-keto-3,3-dimethylhexanoate Utilizing the procedure of EXAMPLE XVI, 29.04 g (0.200 mol) of 2,5-dimethylbenzyl cyanide and 64.88 g (0.300 mol) of diethyl 3,3-dimethyl glutarate were reacted to yield 45.24 g (72%) of ethyl 6-(2',5'-dimelhylphenyl)-6-cyano-5-keto-3,3-dimethylhexanoate as a clear, colorless viscous oil. Structure was confirmed by infrared and nuclear magnetic resonance spectrometry.

IR (neat, μ, principal absorptions): 2.9–3.7 (OH, enol); 4.55 (C=N); 5.80, 5.98, 6.10 (C=O); 6.23 (C=C); 7.35; 7.60; 8.15; 9.70; 12.30.

NMR (CDCl$_3$, δ): 1.18 (multiplet, 9H); 1.67–2.73 (multiplet, 10H); 4.12 (quartet, 2H); 4.88 (singlet 1H); 7.05 (broad, singlet, 3H).

EXAMPLE XXIII

Preparation of 6-(2',5'-Dimethylphenyl)-5-keto-3,3-dimethylhexanoic acid and 2-(2',5'-Dimethylphenyl)-5,5-dimethyl-1,3-cyclohexanedione A solution of 45.24 g (0.14 mol) of ethyl 6-(2',5'-Dimethylphenyl)-6-cyano-5-keto-3,3-dimethylhexanoate, 250 ml of glacial acetic acid. 250 ml of concentrated HCl, and 70 ml of water was refluxed for 48 hours. After 24 hours, an additional 100 ml of concentrated HCl and 150 ml of glacial acetic acid were added.

After 48 hours of refluxing, the reaction mixture was cooled to room temperature and the solvent removed under reduced pressure. The residue was shaken vigorously with 250 ml of water and 250 ml of diisopropyl ether. A white, crystalline precipitate formed which was removed by suction filtration to give 7.90 g (23% yield) of 2-(2'-5'-dimethylphenyl)-5,5-dimethyl-1,3-cyclohexanedione m.p. 168°-170° C.

Calculated for $C_{16}H_{20}O_2$: C, 78.65; H, 8.25. Found: C, 78.16; H, 8.03.

The ether layer was separated from the filtrate, washed once with water, dried over anhydrous $MgSO_4$, and stripped to give 17.97 g of 6-(2',5'-Dimethylphenyl)-5-keto-3,3-dimethyl hexanoic acid as a yellow oil. This oil was not purified, but was characterized by infrared and nuclear magnetic resonance spectrometry.

IR (neat, $\mu$, principal absorptions): 2.9–3.8 (OH); 5.90 (C=O); 12.3 (aromatic).

NMR ($CDCl_3$, $\delta$): 1.08 (singlet, 6H); 2.03 (singlet, 2H); 2.13 (singlet, 2H); 2.27 (singlet, 3H); 2.33 (singlet, 3H); 7.0 (singlet, 3H)

EXAMPLE XXIV

Preparation of Ethyl 6-(2',5'-dimethylphenyl)-5-keto-3,3-dimethylhexanoate

Utilizing the procedure of EXAMPLE XX 6-(2',5'-dimethylphenyl)-5-keto-3,3-dimethyl hexanoic acid was esterified with absolute ethanol in the presence of a catalytic amount of concentrated sulfuric acid to provide 15.52 g (78% yield) of ethyl 6-(2',5'-dimethylphenyl)-5-keto-3,3-dimethylhexanoate as a pale viscous oil.

EXAMPLE XXV

Preparation of 2-(2',5'-Dimethylphenyl)-5,5-dimethyl-1,3-cyclohexanedione

Utilizing the procedure of EXAMPLE XXI, 6-(2',5'-dimethylphenyl-5-keto-3,3-dimethylhexanoate was treated with sodium hydride to yield 9.87 of crude product, which on recrystallization yielded 8.77 g (64%) of 2-(2',5'-dimethylphenyl)-5,5-dimethyl-1,3-cyclohexanedione as a white, crystalline solid m.p. 167°–168° C.

EXAMPLE XXVI

Preparation of 3-(2-Ethylhexanoyloxy)-2-(2'-chlorophenyl)-5,5-dimethyl-2-cyclohexenone A solution of 1.009 (3.99 mmol) of 2-(2'-chlorophenyl)-5,5-dimethyl-1,3-cyclohexanedione and 0.03 g (8.0 mmol) of pyridine was cooled in an ice bath and stirred under $N_2$. The 2-ethylhexanoyl chloride (0.69 g, 4.25 mmol) was added, the mixture was then allowed to warm to room temperature, stirred at room temperature for one hour and refluxed for one hour. The solvent was removed under reduced pressure and the residue taken up in ether and water. The ether was washed three times with 0.25N NaOH, three times with 10% HCl and with water. The ether was dried over anhydrous $MgSO_4$ and decanted to give 1.23 g (82%) of 3-(2'-ethylhexanoyloxy)-2-(2'-chlorophenyl)-5,5-dimethyl-2-cyclohexenone as a clear colorless oil which was homogeneous by thin layer chromatography.

Calculated for $C_{22}H_{29}ClO_3$: C, 70.10; H, 7.76. Found: C, 70:09; H, 7.86.

EXAMPLE XXVII

Preparation of 3-(2'-Ethylhexanoyloxy)-2-(2',4'-dichlorophenyl)-5,5-dimethyl-2-cyclohexenone A solution of 1.76 g (7.02 mmol) of 2-(2',4'-dichlorophenyl)-5,5-dimethyl-1,3-cyclohexanedione in 10 ml of chloroform was cooled in ice and 1.11 g (14.04 mmol) of pyridine added followed by 1.21 g (7.47 mmol) of 2-ethylhexanoyl chloride. The mixture was stirred for 2 hrs. at room temperature and then refluxed for 12 hrs.

The reaction mixture was worked up exactly as described for Example I above to give 2.09 g of a yellow oil. This material was chromatographed using low pressure liquid chromatography on silica gel with a hexane-ethyl acetate gradient to give 1.15 g (41%) of 3-(2'-ethylhexanoyloxy)-2-(2',4'-dichlorophenyl)-5,5-dimethyl-2-cyclohexenone as a clear, colorless oil. The thin layer chromatogram (80:20 hexane-ethyl acetate) of this material showed one spot at Rf=0.46.

Calculated for $C_{22}H_{28}Cl_2O_3$: C, 64.23; H, 6.86. Found: C, 64.44; H, 6.80.

EXAMPLE XXVIII

Preparation of 3-hexanoyloxy-5,5-dimethyl-2-(2',4'-dimethylphenyl)-2-cyclohexenone A solution of 1.50 g (6.14 mmol) of 2-(2',4'-dimethylphenyl)-5,5-dimethyl-1,3-cyclohexanedione in 10 ml of chloroform was cooled in ice and 1.94 g (24.56 mmol) of pyridine added followed by 1.64 g (12.28 mmol) of hexanoyl chloride. The mixture was stirred for 2 hrs. at room temperature, then refluxed for 5 hrs.

The reaction mixture was cooled to room temperature and taken up in 150 ml of ether. The ether was washed three times with 50 ml of 0.25N NaOH, twice with 50 ml portions of ice cold 6N HCl, and twice with water. The ether was dried over anhydrous ($MgSO_4$) and removed under reduced pressure to leave 0.98 g (47% yield) 3-hexanoyloxy-5,5-dimethyl-2-(2',4'-dimethylphenyl)-2-cyclohexenone as a clear, colorless oil. This oil showed one spot on a thin layer chromatogram (70:30 hexane-ethyl acetate) at Rf=0.49.

Calculated for $C_{22}H_{30}O_3$: C, 77.15; H, 8.83. Found: C, 77.25; H, 8.92.

EXAMPLE XXIX

Preparation of 3-(2-Ethylhexanoyloxy)-5,5-dimethyl-2(2',4'-dimethylphenyl)-2-cyclohexenone A solution of 1.50 g (6.14 mmol) of 2-(2',4'-dimethylphenyl)-5,5-dimethyl-1,3-cyclohexanedione in 10 ml of chloroform was cooled in ice and 1.94 g (24.56 mmol) of pyridine added followed by 2.00 g (12.28 mmol) of 2-ethylhexanoyl chloride. The mixture was stirred for 2 hrs. at room temperature, then refluxed for 12 hrs. The mixture was worked up exactly as described in Example I above to give 1.58 g of a slightly yellow, viscous oil. This material was chromatographed through 75 g of silica gel (0.063–0.2 mm) using a gradient ranging from 98:2 to 90:10 hexane-ethyl acetate. The chromatography gave 1.15 g (51%) of 3-(2-ethylhexanoyloxy)-5,5-dimethyl-2-(2',4'-dimethylphenyl)-2-cyclohexenone as a clear colorless oil which showed one spot on a thin layer chromatogram (70:30 hexane-ethyl acetate) at Rf=0.52.

Calculated for: $C_{24}H_{34}O_3$: C, 77.80; H, 9.25. Found: C, 77.34; H, 9.48.

EXAMPLE XXX

Preparation of
3-Hexanoyloxy-2-(2',4'-dichlorophenyl)-5,5-dimethyl-2-cyclohexenone A solution of 2.00 g (8.00 mmol) of 2-(2',4'-dichlorophenyl)-5,5-dimethyl-1,3-cyclohexanedione in 10 ml of chloroform was cooled in ice and 1.26 g (16.00 mmol) of pyridine was added followed by 1.14 g (8.50 mmol) of hexanoyl chloride. The mixture was stirred for 2 hrs. at room temperature and refluxed for 12 hrs.

The reaction mixture was worked up exactly as described for Example I above to give 1.94 g of a slightly yellow oil. This material was chromatographed using a low pressure liquid chromatography system and a hexane-ethyl acetate gradient. Work-up of the chromatography gave 1.55 g (51% yield) of 3-hexanoyloxy-2-(2',4'-dichlorophenyl)-5,5-dimethyl-2-cyclohexenone as a clear, colorless oil which on a thin layer chromatogram (80:20 hexane-ethyl acetate) showed one spot at Rf=0.27.

Calculated for: $C_{20}H_{24}Cl_2O_3$: C, 62.67; H, 6.31. Found: C, 62.83; H, 6.32.

EXAMPLE XXXI

Preparation of
3-(2-Ethylhexanoyloxy)-5,5-dimethyl-2-(2',5'-dimethylphenyl)-2-cyclohexenone A suspension of 1.50 g (6.14 mmol) of 2-(2',5'-dimethylphenyl)-5,5-dimethyl-1,3-cyclohexanedione in 15 ml of dry benzene was prepared and 0.49 g (7.37 mmol) of 85% powered potassium hydroxide was added, followed by 1 drop of dicyclohexyl-18-crown-6-ether. After stirring for 30 minutes, 1.20 (7.37 mmol) of 2-ethylhexanoyl chloride was added, and the reaction mixture refluxed for 12 hrs. The reaction mixture was cooled to room temperature, taken up in 150 ml ether and 50 ml of water, washed three times with 0.25N NaOH, two times with water, two times with 6N HCl, and one more with water. The ether solution was dried and stripped to leave 2.10 g (92% yield) of 3-(2-ethylhexanoyloxy)-5,5-dimethyl-2-(2',5'-dimethylphenyl)-2-cyclohexenone as a clear, colorless oil.

Calculated for: $C_{24}H_{34}O_3$: C, 77.80; H, 9.25. Found: C, 77.46, H, 8.98.

EXAMPLE XXXII

Preparation of
2-(2',4'-Dimethylphenyl)-1,3-cyclohexanedione

A 500 ml 3-neck round bottom flask was equipped with a mechanical stirrer, addition funnel, and reflux condenser. The glassware was dried thoroughly and the flask charged with 4.62 g (0.096 g-atom) of 50% sodium hydride in mineral oil. The oil was washed off the NaH using toluene, and then 100 ml of toluene added. The mixture was warmed to 65° C. and 12.62 g (0.0481 mol) ethyl 6-(2',4'-dimethylphenyl)-5-ketohexanoate added, dropwise, over a 2 hr. period. The mixture was maintained at 65° C. for 12 hrs., then carefully quenched with 25 ml of ice water. The reaction mixture was diluted with 250 ml of water and extracted twice with 150 ml of ether. The aqueous base solution was acidified to pH=3 with 6N HCl, and extracted twice with 150 ml of methylene chloride. The methylene chloride was washed with water, dried over anhydrous $MgSO_4$ and stripped to give 5.88 g of a semi-solid. This was recrystallized from ethyl acetate to give 5.10 g (49%) of 2-(2',4'-dimethylphenyl)-1,3-cyclohexanedione as a white, crystalline solid, m.p. 143°–145° C.

Calculated for: $C_{14}H_{16}O_2$: C, 77.75; H, 7.46. Found: C, 76.99; H, 7.46.

EXAMPLE XXXIII

Preparation of
2-(2'-Chlorophenyl)-1,3-cyclohexanedione

A 500 ml one-neck round bottom flask was charged with 10.0 g (0.0416 mol) of 6-(2'-chlorophenyl)-5-ketohexanoic acid and 100 ml of 72% sulfuric acid. The reaction mixture was stirred and heated to 120° C. for 5¼ hrs. (oil bath) then poured into 600 ml of ice water. A tacky, white solid formed, and this was extracted into 300 ml of methylene chloride. The $CH_2Cl_2$ solution was washed six times with water, dried over anhydrous $MgSO_4$, and stripped to leave 8.87 g of a tacky, white solid. This material was recrystallized from ethyl acetate to give 5.85 g (63%) of 2-(2'-Chlorophenyl)-1,3-cyclohexanedione as a white, crystalline solid, m.p. 148.5°–149° C.

Calculated for: $C_{12}H_{11}ClO_2$: C, 64,73; H, 4.98. Found: C, 64.49; H, 4.89.

EXAMPLE XXXIV

Preparation of
2-(2'-Chloro-4'-nitrophenyl)-5,5-dimethyl-1,3-cyclohexanedione

A solution containing 42.05 g (0.300 mol) of 5,5-dimethyl-1,3-cyclohexanedione and 100 g (0.718 g-atom) of anhydrous potassium carbonate in 300 ml of dry dimethylformamide was heated to 75° C. under nitrogen and stirred for one hour. The 3,4-dichloronitrobenzene, 57.60 g (0.300 mol) was dissolved in 100 ml dmethylformamide and added dropwise to the reaction mixture while stirring and maintaining the temperature of the reaction mixture at 75°. A deep red-colored solution formed, and when the addition was complete the reaction temperature was raised to 100° C. and held at this temperature for 3 hours. Most of the dimethylformamide was removed by vacuum distillation. The residue was poured into 21 of ice water and extracted three times with 500 ml of benzene. Nitrogen was then passed through the aqueous solution while warming to remove dissolved benzene. The aqueous solution was cooled in an ice bath and acidified to give a tacky precipitate, which, upon warming solidified and was collected by suction filtration. The reaction product was recrystallized from acetone to give 31.7 g (36%) of 2-(2'-Chloro-4'-nitrophenyl)-5,5-dimethyl-1,3-cyclohexanedione as a white powder, m.p. 250°–253° C.

Calculated for: $C_{14}H_{14}ClNO_4.1/2H_2O$: C, 55.18 H, 4.96; N, 4.60. Found: C, 55.53; H, 4.73; N, 5.09.

EXAMPLE XXXV

Preparation of
2-(2'-Chloro-4'-aminophenyl)-5,5-dimethyl-1,3-cyclohexanedione

A solution of 20.0 g (0.067 mol) of 2-(2'-chloro-4'-nitrophenyl)-5,5-dimethyl-1,3-cyclohexanedione in 150 ml of concentrated ammonium hydroxide and 150 ml of ethanol was stirred at room temperature while passing hydrogen sulfide gas through the solution at such a rate that all of the $H_2S$ was absorbed. When the solution was saturated with $H_2S$, the temperature was raised to the reflux point and $H_2S$ continuously passed slowly through the refluxing solution for 24 hours. The reaction mixture was filtered to remove sulfur, and the filtrate evaporated under reduced pressure. To the residue was added 300 ml of 0.25N NaOH, and the solution filtered once more. The filtrate was cooled and carefully acidified to pH=4 with 6NHCl. A white solid formed which was collected by suction filtration to give 13.3 g (74%) of 2-(2'-Chloro-4'-aminophenyl)-5,5-dimethyl-1,3-cyclohexanedione, m.p. 218°-219° C.

Calculated for: $C_{14}H_{16}ClNO_2.1/2H_2O$: C, 61.20; H, 6.24; N, 5.10. Found: C, 60.44; H, 5.83; N, 5.32.

EXAMPLE XXXVI

Preparation of 2-(2'-Chlorophenyl)-5,5-dimethyl-1,3-cyclohexanedione

The 2-(2'-chloro-4'-aminophenyl)-5,5-dimethyl-1,3-cyclohexanedione (9.66 g. 0.0364 mol) was added to 7.0 ml of concentrated HCl in 150 ml of water, and the mixture stirred and heated almost to boiling. An additional 15.0 ml of HCl was added and the mixture cooled to 0°-5° C. A solution of 3.22 g (0.0467 mol) of sodium nitrite in 9.0 ml of water was added dropwise while the reaction mixture was stirred and maintained at 0°-5° C. When addition of the sodium nitrite solution was complete, the reaction mixture was stirred at 0°-5° C. for one hour.

The diazonium salt solution prepared above was added in portions to 161 ml of 50% hypophosphorous acid at 0° C., with stirring and cooling. The reaction mixture was stirred for 12 hours and filtered to give 8.55 g of a tan solid. This maternal was chromatographed through 250 g of Woelm silica gel (0.063-0.2 mm) eluting with a gradient from pure benzene to 70:30 benzene-ethyl acetate. A total of 7.12 g of product was obtained from the chromatography and recrystallized from benzene-ethyl acetate to give 6.85 g (75%) of 2-(2'-Chlorophenyl)-5,5-dimethyl-1,3-cyclohexanedione as white crystals, m.p. 191°-192° C.

Calculated for: $C_{14}H_{15}C_1O_2$: C, 67.07; H, 6.03. Found: C, 67.04; H, 6.00.

EXAMPLE XXXVII

Preparation of 2-(2',4'-6'-Trimethylphenyl)-cyclohexane-1,3-dione

A solution of 5.00 g (0.036 mol) of 2-diazocyclohexane-1,3-dione in 500 ml of mesitylene (dry, distilled) containing 32.8 g (0.18 mol) benzophenone was degassed with nitrogen for one hour, and irradiated with a 200 watt Hanovia immersion lamp through a borosilicate glass filter, until the complete disappearance of the diazo band (4.68μ) in the infrared was observed. The reaction was also monitored by thin layer chromatography (90:10 ethyl acetate-benzene) and irradiation continued until no diazoketone at $R_f=0.31$ could be seen. The irradiation required 11 hours. The mesitylene was extracted with 0.25N sodium hdroxide until a small aliquot showed no cloudiness upon acidification. The combined base extracts were washed twice with 200 ml of ether, and acidified (pH=5) with 1N HCl. The aqueous solution was extracted three times with 75 ml portions of chloroform, dried over anhydrous $MgSO_4$, and the solvent stripped to give 5.06 g of a tan solid.

This solid was chromatographed through 250 g of silica gel (0.065-1.2 mm) eluting with a gradient from pure benzene to 80:20 benzene-ethyl acetate. A total of 2.60 g (31%) of a white solid (homogeneous by thin layer chromatography) was obtained and recrystallized from diisopropyl ether to give 1.96 g of 2-(2',4',6'-trimethylphenyl)-1,3-cyclohexanedione as white crystals, mp 196°-198° C.

Calculated for: $C_{15}H_{18}O_2$: C, 78.23; H, 7.88. Found: C, 77.94; H, 8.20.

Selected species of the new compositions were evaluated to determine their pesticidal activity against certain insects, including the Housefly southern armyworm and bollworm larvae.

EXAMPLE XXXVIII

Use of a Mixture of 3(2-Ethylhexanoyloxy)-5,5-Dimethyl-2-(2',4'-Dimethylphenyl)-2-Cyclohexenone and Carbaryl for Control of the Common Housefly, *Musca domestica*, (L.)

Suspensions of the dione ester of Example XXIX, carbaryl, and a mixture containing the dione ester of Example XXIX plus carbaryl were prepared by dissolving, in separate beakers, one gram of each compound in 50 milliliters of acetone in which had been dissolved 0.1 gram (10 percent by weight of the compound) of an alkylphenoxy polyethoxyethanol surfactant, as an emulsifying or dispersing agent. The resulting solution was mixed into 150 milliliters of a solution containing 10 grams of sugar in 100 ml of water to give 200 milliliters of a suspension containing each compound in finely divided form. The thus-prepared stock suspensions contained 0.5 percent by weight of each compound. The concentrations employed in the test described herein below were obtained by diluting the stock suspension with sugar water. Dilution tests were conducted to determine the $LD_{50}$ (concentration required to kill 50 percent of the housefly population) of carbaryl and of a mixture of carbaryl and the dione ester of Example XXIX. A 10 milliliter volume of the test formulation containing 500 ppm of the dione ester of Example XXIX in sugar water was transferred to a soufflé cup containing a one-inch square pad of absorbent cotton. Similar baits were prepared with 10 ml. volume of test formulations of carbaryl. The test concentrations of carbaryl were 500 ppm, 250 ppm and 125 ppm. The stock suspension of carbaryl was diluted with appropriate amounts of the stock suspension of the dione ester to provide a series of concentration ranging from 500 ppm of carbaryl plus 500 ppm of the dione of Example XXIX to 60 ppm of carbaryl plus 500 ppm of the dione ester of Example XXIX. Four to six day old adult houseflies were reared according to the specifications of the Chemical Specialties Manufacturing Association, [Blue Book, (McNair-Dorland Company, New York) pp. 243-244, 261, 1954] under controlled conditions of 80±5° F. and 50±5 percent relative humidity. The adult flies were immobilized by anesthetizing with $CO_2$. Twenty-five immobilized individuals (males and females) were then transferred to a cage consisting of a standard food strainer approximately 5 inches in diameter which was then inverted over kraft paper containing the bait cup.

The caged flies were allowed to feed on the bait for a period of 24 hours. Room temperature and humidity during the 24 hours were 80±5° F. and 50±5 percent relative humidity. At 24 hours the flies which showed no sign of movement upon stimulation were considered dead. The results of these tests are set forth in Table I.

TABLE I

Toxicity to Housefly adults of the dione ester of Example XXIX, carbaryl and a mixture containing the dione ester of Example XXIX and carbaryl.

| % Kill Obtained with 500 ppm of The Dione Ester | Carbaryl LD$_{50}$ PPM Alone | Carbaryl Plus 500 ppm of Dione Ester |
|---|---|---|
| 0 | 360 | 90 |

The mixture of carbaryl and the dione ester of Example XXIX produces surprising synergistic kill of the housefly.

EXAMPLE XXXIX

Use of Mixtures of Dione Esters and Permethrin, Decamethrin, Methyl Parathion and Sulprofos for Control of Southern Armyworm Larvae (*Spodoptera eridania*) (Cramer)

Aqueous suspension of dione esters, permethrin, decamethrin, methyl parathion and sulprofos were prepared by dissolving one gram of each compound in 50 milliliters of acetone in which had been dissolved 0.1 gram (10 percent by weight of each compound to be tested) of an alkylphenoxy polyethoxyethanol surfactant as an emulsifying or dispersing agent. The resulting solutions were mixed with 150 milliliters of water to give 200 milliliters of a suspension containing each test compound in finely divided form. The thus-prepared stock suspension contained 0.5 percent by weight of each compound. Potted tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

The concentration employed in the test results presented below were obtained by diluting the stock suspensions with water. Dilution tests were conducted to determined the LD$_{50}$ (concentration required to kill 50 percent of the armyworm larvae). The results of these tests are set forth in Table II.

TABLE II

| | Toxicity To Armyworm Larvae | | | |
|---|---|---|---|---|
| | | % Kill, | LD$_{50}$, PPM | |
| Pesticide Name | Dione Ester | 500 ppm dione ester | Pesticide Alone | Pesticide Plus 500 ppm of dione ester |
| fenvalerate | [structure: cyclohexenone with two CH$_3$ groups, phenyl with ortho-CH$_3$ and OC(=O)CH(CH$_2$)$_3$CH$_3$ with OC$_2$H$_5$] | 0 | 3.2 | 1.1 |
| permethrin | " | 0 | 3.2 | 2.2 |
| decamethrin | " | 0 | 0.2 | 0.1 |
| methyl parathion | " | 0 | 17 | 9 |
| sulprofos | " | 0 | 19 | 11 |
| fenvalerate | [structure: cyclohexenone with two CH$_3$ groups, phenyl with ortho-CH$_3$, para-CH$_3$ and OCCH(CH$_2$)CH$_3$ with OC$_2$H$_5$] | 10 | 2.5 | 0.6 |
| permethrin | " | 15 | 3 | 1.5 |
| fenvalerate | [structure: cyclohexenone with two CH$_3$ groups, phenyl with para-CH$_3$ and OCCH(CH$_2$)$_3$CH$_3$ with OC$_2$H$_5$] | 0 | 4 | 1 |

TABLE II-continued

| | Toxicity To Armyworm Larvae | | | |
|---|---|---|---|---|
| | | % Kill, | LD$_{50}$, PPM | |
| Pesticide Name | Dione Ester | 500 ppm dione ester | Pesticide Alone | Pesticide Plus 500 ppm of dione ester |
| fenvalerate | 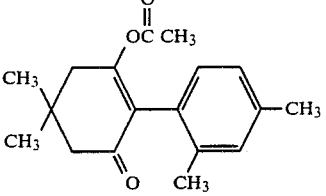 | 0 | 4 | 2 |

Mixtures of the dione esters of Example XXXIX and fenvalerate, permethrin decamethrin, methyl parathion and sulprofos clearly given synergistic kill of armyworm larvae.

EXAMPLE XL

Use of a Mixture of 3-(2-Ethylhexanyloxy)-5,5-Dimethyl-2-(2',4'-Dimethylphenyl)-2-Cyclohexenone and Fenvalerate for Control of Bollworm (*Heliothis zea.*) (Boddie)

The test method employed in determining the synergistic kill of mixtures of the dione ester of Example XL and fenvalerate to the bollworm were identical to those described in Example XXXIX except that cotton seedlings instead of beam seedlings were sprayed with the aqueous suspensions of the test formulations and bollworm larvae rather than armyworm larvae were used as test insects. Since bollworm larvae are canibalistic only 1 larvae was enclosed in each petri plate and 10 petri plates each containing a cotton leaf were used. The results of these tests are set forth in Table III.

TABLE III

| | Toxicity to Bollworm Larvae | | | |
|---|---|---|---|---|
| | | % Kill | LD$_{50}$, PPM | |
| Pesticide Name | Dione Ester | 500 ppm dione ester | Pesticide Alone | Pesticide plus 500 ppm of dione ester |
| fenvalerate | 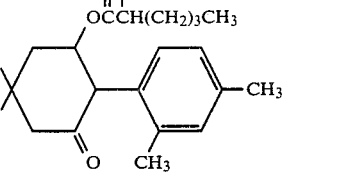 | 0 | 10 | 4 |

Mixtures of the dione ester of Example XL and fenvalerate clearly show surprising synergistic kill of bollworm larvae.

It will be understood that the insect species employed in the tests are representative of a wide variety of insects that can be controlled by the methods of this invention. The methods of this invention can be used to control insects which attack plants or warm-blooded animals, stored products and fabrics. Representative of crop plants that can be so treated are cotton, corn, rice, wheat soybean, fruits and ornamental plants and the like. Representative of animals that can be protected by the methods of this invention are man, horses, dogs, cats, cattle, sheep, goats, hogs and the like. Representative of stored products that can be protected from insect attack by the methods of this invention are grains, flour and flour products, tobacco and tobacco products, processed foods and the like. Representative of fabrics that can be protected from insect attack by the methods of this invention are wool, cotton, silk, linen and the like.

The results set forth above clearly show the broad spectrum pesticidal activity of the compounds of this invention.

The compounds contemplated in this invention may be applied according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a non-phytotoxic solvent such as acetone, xylene or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Non-ionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to 90 percent by weight. Satisfactory sprays, dusts, or granules for general use contain from about ¼ to 15 pounds of active toxicant per acre.

The pesticides contemplated herein prevent attack by insects, upon plants or other material to which the pesticides are applied, and they have relatively high residual toxicity. With respect to plants, they have a high margin of safety in that when used in sufficient amount to kill or repel insects, they do not burn or injure the plant, and they resist weathering which includes wash-off caused by rain, decomposition by ultra-violet light, oxidation, or hydrolysis in the presence of moisture or, at least such decomposition, oxidation and hydrolysis as would materially decrease the desirable pesticidal characteristic of the toxicants or impart undesirable characteristics, for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds.

Although the invention has been illustrated by the preceding examples, it is not to be construed as being limited to the materials employed herein, but rather, the invention encompasses the generic area as hereinbefore disclosed. Various modifications and embodiments can be made without departing from the spirit and scope thereof.

What is claimed is:

1. An insecticidal composition consisting essentially of an acceptable carrier and as the active toxicant therefor, a mixture of:

(a) a first compound selected from

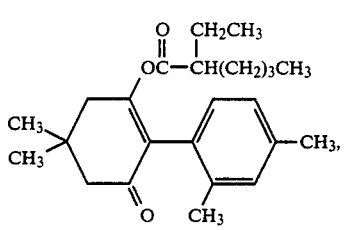

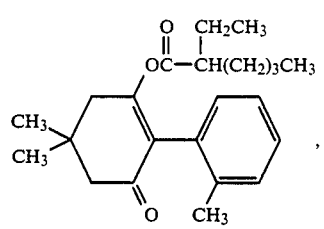

-continued

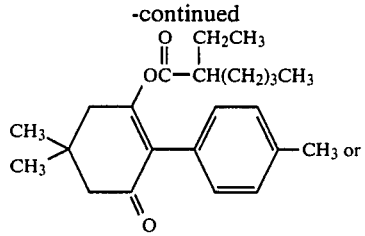

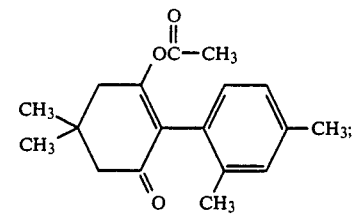

and (b) a second compound selected from

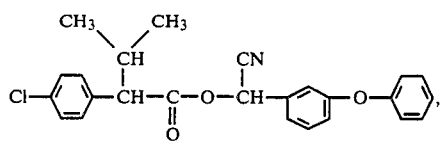

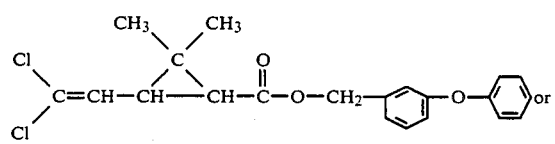

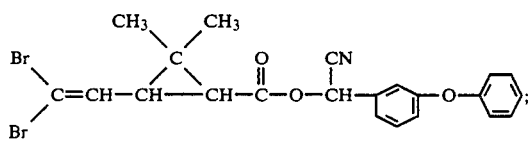

said first and second compound are present in a respective weight ratio of from about 500:1 to about 1:1.

2. The composition of claim 1 wherein said first and second compound are present in a respective weight ratio of from about 100:1 to about 10:1.

3. The composition of claim 1 wherein said first compound has the formula

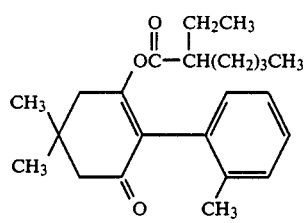

and said second compound has the formula

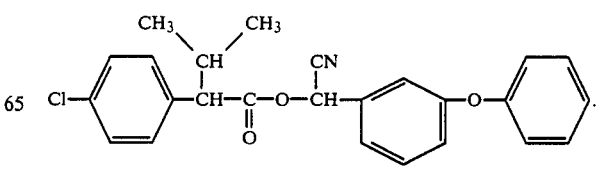

4. The composition of claim 1 wherein said first compound has the formula

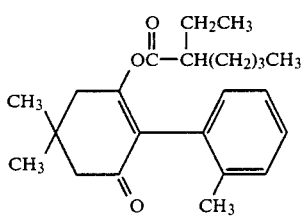

and said second compound has the formula

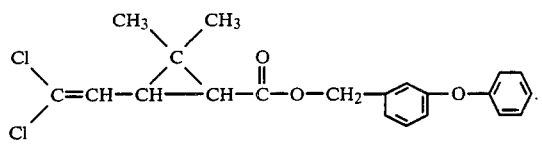

5. The composition of claim 1 wherein said first compound has the formula

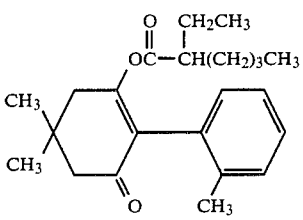

and said second compound has the formula

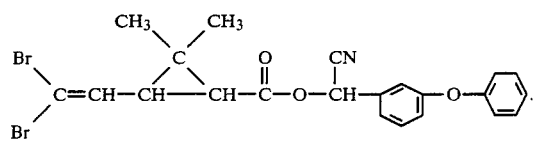

6. The composition of claim 1 where said first compound has the formula

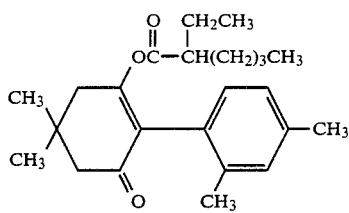

and said second compound has the formula

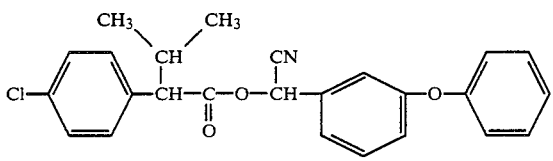

7. The composition of claim 1 wherein said first compound has the formula

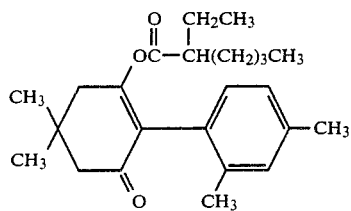

and said second compound has the formula

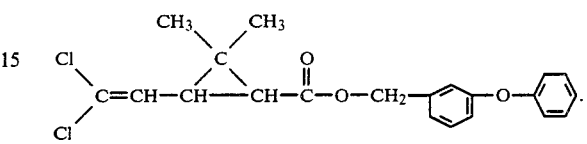

8. The composition of claim 1 wherein said first compound has the formula

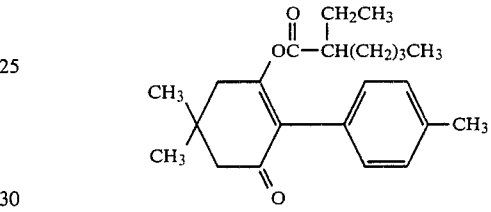

and said second compound has the formula

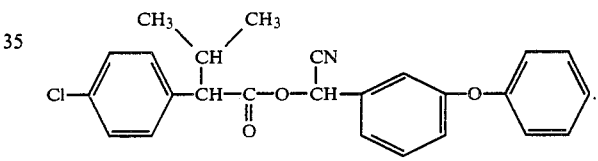

9. The composition of claim 1 wherein said first compound has the formula

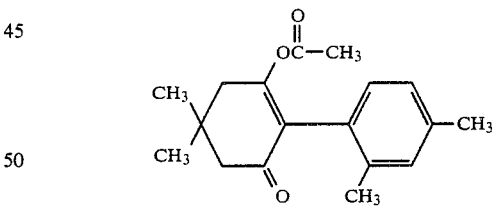

and said second compound has the formula

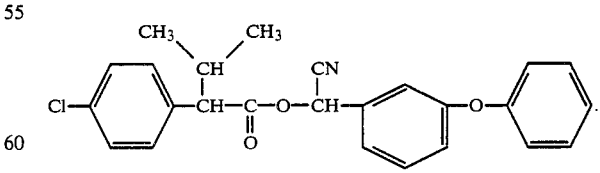

10. A method for controlling insects which comprises contacting said insects with an insecticidally effective amount of the composition of claim 1.

* * * * *